United States Patent [19]

Wood et al.

[11] Patent Number: 5,351,305
[45] Date of Patent: Sep. 27, 1994

[54] CONCURRENT SMOOTHING AND EDGE ENHANCEMENT OF MEDICAL DIAGNOSTIC IMAGES

[75] Inventors: Christopher H. Wood, Cleveland; Fares Hajjar, Cleveland Hts.; Anthony Apicella, Willoughby; Kevin E. Matthews, Brecksville, all of Ohio

[73] Assignee: Picker International, Inc., Highland Hts., Ohio

[21] Appl. No.: 893,785

[22] Filed: Jun. 5, 1992

Related U.S. Application Data

[63] Continuation-in-part of Ser. No. 791,855, Nov. 14, 1991, Pat. No. 5,273,040.

[51] Int. Cl.$^5$ ............................................. G06K 9/40
[52] U.S. Cl. ...................................... 382/6; 382/22; 382/54; 364/413.13
[58] Field of Search ........................... 382/6, 22, 54; 364/413.19, 413.13; 324/312

[56] References Cited

U.S. PATENT DOCUMENTS

| | | | |
|---|---|---|---|
| 4,499,493 | 2/1985 | Nishimura | 364/413.19 |
| 4,503,461 | 3/1985 | Nishimura | 364/413.19 |
| 4,691,366 | 9/1987 | Fenster et al. | 382/54 |
| 4,761,819 | 8/1988 | Denison et al. | 382/54 |
| 4,834,964 | 5/1989 | Rosen | 424/9 |
| 4,851,678 | 7/1989 | Adachi et al. | 382/6 |
| 4,972,256 | 11/1990 | Hirosawa et al. | 358/80 |
| 4,991,092 | 2/1991 | Greensite | 364/413.13 |
| 5,001,429 | 3/1991 | Constable et al. | 324/312 |
| 5,031,227 | 7/1991 | Raasch et al. | 382/22 |
| 5,050,227 | 9/1991 | Furusawa et al. | 382/22 |
| 5,063,607 | 11/1991 | FitzHenry et al. | 382/50 |
| 5,072,314 | 12/1991 | Chang | 359/559 |
| 5,078,141 | 1/1992 | Suzuki et al. | 128/653.2 |
| 5,081,692 | 1/1992 | Kwon et al. | 382/54 |
| 5,115,476 | 5/1992 | Ito | 382/22 |
| 5,157,741 | 10/1992 | Katayama | 382/54 |
| 5,218,649 | 6/1993 | Kundo et al. | 382/54 |

OTHER PUBLICATIONS

Digital Picture Processing, Rosenfeld, et al. Second Edition, vol. 1, 1982 Academic Press, Inc. pp. 245-267.
Adaptive Smoothing: A General Tool for Early Vision, Saint-Marc, et al. IEEE vol. 13, No. 6, Jun. 1991, pp. 514-529.

*Primary Examiner*—Leo H. Boudreau
*Assistant Examiner*—Christopher S. Kelley
*Attorney, Agent, or Firm*—Fay, Sharpe, Beall, Fagan, Minnich & McKee

[57] ABSTRACT

A magnetic resonance imaging system (A) generates an image (16) of a slice or other region of an examined subject. A smoothing filter (B) smooths the generated image to create a smoothed or filtered image representation (30). The filtering of the image, unfortunately, tends to smooth or blur the edges. An edge detecting means ($C_1$) views the region around each sampled pixel of the filtered image to determine an amount of deviation in the pixel values. A large deviation indicates an edge; whereas, substantial homogeneity indicates the lack of an edge. Analogously, the direction of the maximum deviation is orthogonal to the direction of the edge. A plurality of soft edge directional filters (54) operate on the filtered image data to create a plurality of soft edge directionally filtered image representations (62). A plurality of hard edge directional filters (56) operate on the filtered image data to create a plurality of hard edge directionally filtered image representations (64). Preferably, the directional filtering is done at regular angular increments, e.g. every ten degrees. An edge enhanced final image representation (72) is created in which filtered pixels not adjacent an edge are assembled directly from the filtered image (30). Pixels which are adjacent an edge with a smaller (larger) rate of deviation are replaced by the corresponding pixel of the soft (hard) edge filtered image representation that was directionally filtered along a direction most nearly parallel to the determined edge direction.

9 Claims, 2 Drawing Sheets

CONCURRENT SMOOTHING AND EDGE ENHANCEMENT OF MEDICAL DIAGNOSTIC IMAGES

This application is a continuation-in-part of U.S. patent application Ser. No. 07/791,855, filed Nov. 14, 1991, now U.S. Pat. No. 5,273,040.

BACKGROUND OF THE INVENTION

The present invention relates to the image processing arts. It finds particular application in conjunction with improving the diagnostic value of magnetic resonance medical diagnostic images and will be described with particular reference thereto. It is to be appreciated that the invention will also find application in conjunction with improving other medical diagnostic images such as CT, digital x-ray, nuclear camera, ultrasound, and the like, as well as non-medical electronic images such as television images, radio telescope, and the like.

Medical diagnostic images are commonly subject to degradation from noise, system imperfections, and the like. One technique for improving diagnostic images is to acquire redundant data, e.g. the data for two or more images and averaging or summing to reduce the effects of random noise or error. However, multiple data acquisitions are time consuming and expensive. Moreover, in regions of patient motion, averaging may blur rather than improve the resultant image.

Others have attempted to improve the imagability of the subject by injecting contrast agents into the patient. See for example, U.S. Pat. No. 4,834,964 of Rosen. However, injected contrast agents only improve limited image characteristics. As an invasive technique, it is sometimes inappropriate for medical reasons.

The acquired images can be processed with modifications to the histogram or distribution of signal values on a global or local basis. See for example, U.S. Pat. No. 5,063,607 of FitzHenry. In other techniques, the gray scale range of each subimage region is stretched such that it covers the entire display range. See for example, U.S. Pat. No. 4,991,092. However, histogram modifications by attempting to expand the dynamic range of the data, increase the noise in the image. Local histogram modifications cause a blocking effect on the resultant image. That is, the processing of the various subregions of the image with different histogram modifications tends to result in a lack of uniformity over the entire image.

Others have also enhanced images using convolution or filtering techniques. Such techniques include the selective amplification of selected frequency bands as illustrated in U.S. Pat. No. 5,072,314 of Chang. Others have used a combination of high and low pass filtering to enhance images as illustrated for example in U.S. Pat. No. 5,081,692 to Kwon or U.S. Pat. No. 4,972,256 to Hirosawa. However, global filtering techniques tend to blur the images and eliminate the lower frequency regions. This makes evaluation of the images difficult.

To eliminate some of the drawbacks of a global filtering or convolution, others have used locally adjusted filtering. See for example, U.S. Pat. No. 4,761,819 of Denison, et al., U.S. Pat. No. 4,991,092 of Kwon, U.S. Pat. No. 5,050,227 of Furusawa, and "Adaptive Smoothing: A General Tool For Early Vision", IEEE Transactions on Pattern Analysis and Machine Intelligence, Vol. 13, No. 6, Jun. 1991, Saint-Marc, et al. However, the local filtering techniques had difficulty distinguishing between sudden image variations attributable to edges and sudden image variations attributable to noise. These techniques also fail to account for differences in edge direction and regional variance, producing an image which is overly smooth without consideration of the edges. That is, they tend to blur the image.

Still others have attempted restoration approaches in which the acquisition process was modeled and the degradations of the imaging process described mathematically. These techniques then attempted to invert the degradations using restoration techniques such as least squares, Bayesian, or Kahlman filtering. However, the restoration methods required a model for the acquisition process. Complicated acquisition processes, such as MRI imaging, were too difficult to model accurately. Moreover, computing the parameters of a complicated model for a given image can require iterative algorithms which have a great computational expense.

U.S. Pat. No. 4,691,366 of Fenster, et al. uses filters which are adjusted to enhance long edges and attenuate noise and points. However, this techniques requires an analysis of the imaging system in order to produce the appropriate filters. Such analysis is time consuming and prone to errors.

The present invention provides a new and improved imaging technique which overcomes the above-referenced problems and others.

SUMMARY OF THE INVENTION

In accordance with one aspect of the present invention, an image is transformed into the frequency domain and filtered with each of a plurality of directional filters. The area around each pixel is examined to determine proximity of the pixel to an edge, and, if proximate to an edge, the angle of the edge. In the final image, each pixel that is proximate an edge is replaced by the corresponding pixel of an image processed with the one of the directional filters whose direction and edge properties are most similar to the direction and edge properties of the proximate edge.

In accordance with another aspect of the present invention, a rate of change at each edge is determined. A directional filter with more or less filtering, i.e. a hard or soft filter, is selected in accordance with the rate of change of the edge.

More specifically to the preferred embodiment, the frequency domain data is transformed with both hard and soft directional filters for each of a multiplicity of angles or directions and the filtered data reconstructed into corresponding images. For each pixel that is determined to be sufficiently proximate to an edge, one of the hard or soft filtered groups of images are selected. Within the selected group of images, the corresponding pixel from the image whose filter direction most closely corresponds to the direction of the edge is selected.

In accordance with another aspect of the present invention, an initial noise reduction operation is performed to smooth non-edge portions and improve angle and rate of change calculations.

One advantage of the present invention is that it can be used in conjunction with existing equipment. No modifications or additions to traditional data acquisition techniques are required.

Another advantage of the present invention is that it does not increase data acquisition time.

Another advantage of the present invention is that it produces better quality images. It produces images that are smooth across regions of homogeneity while preserving edges, regardless of their size or direction. By smoothing along the direction of the edges, the boundaries of image regions are not compromised.

Another advantage of the present invention is that no a priori knowledge about the image or data acquisition techniques is required. A selected filter is self or autotuning.

The imaging process is relatively time efficient. No iterative modeling processing is needed.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1A:
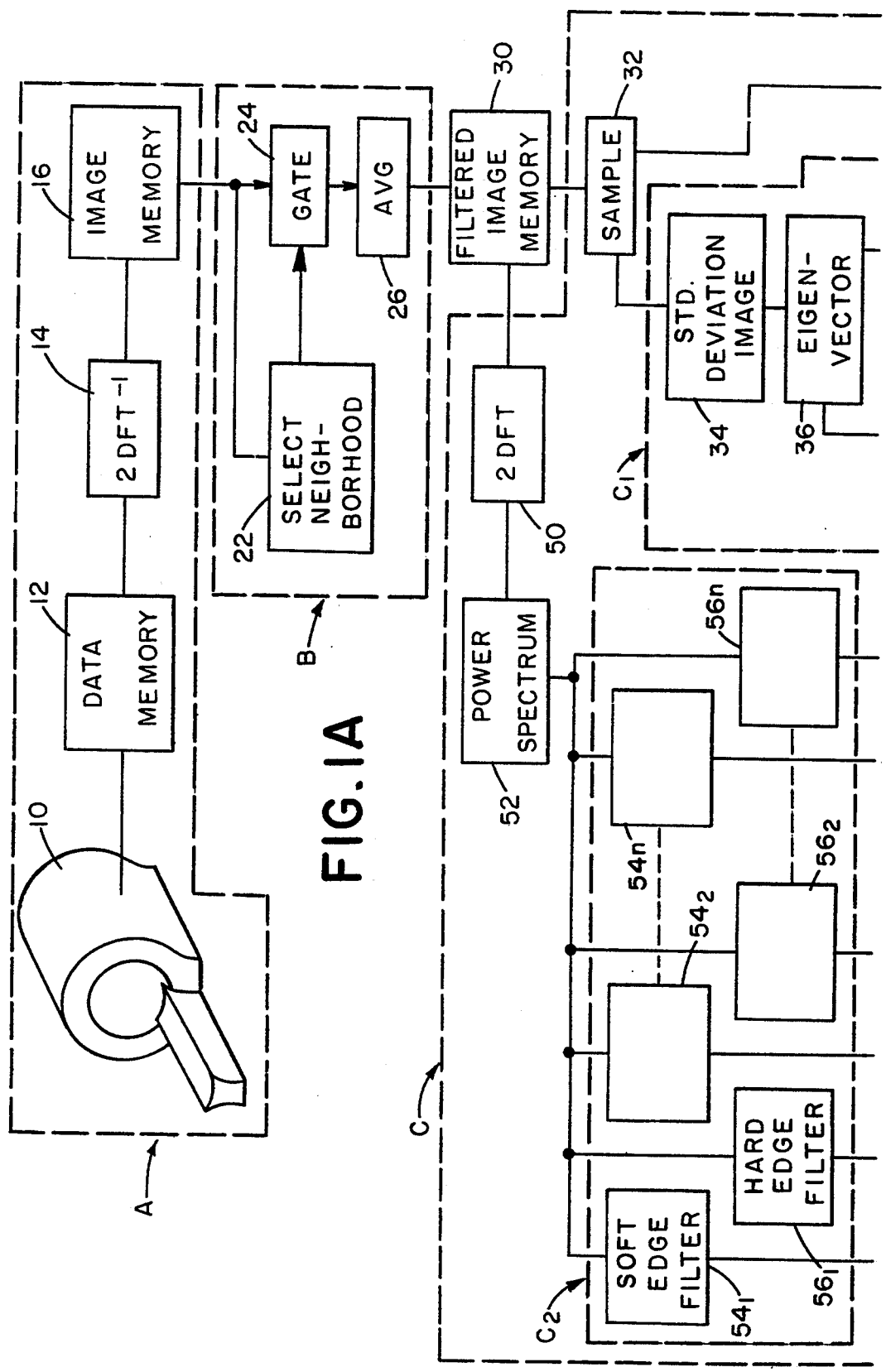
FIGS. 1A and 1B taken together are a diagrammatic illustration of the present invention.
Figure 1B:
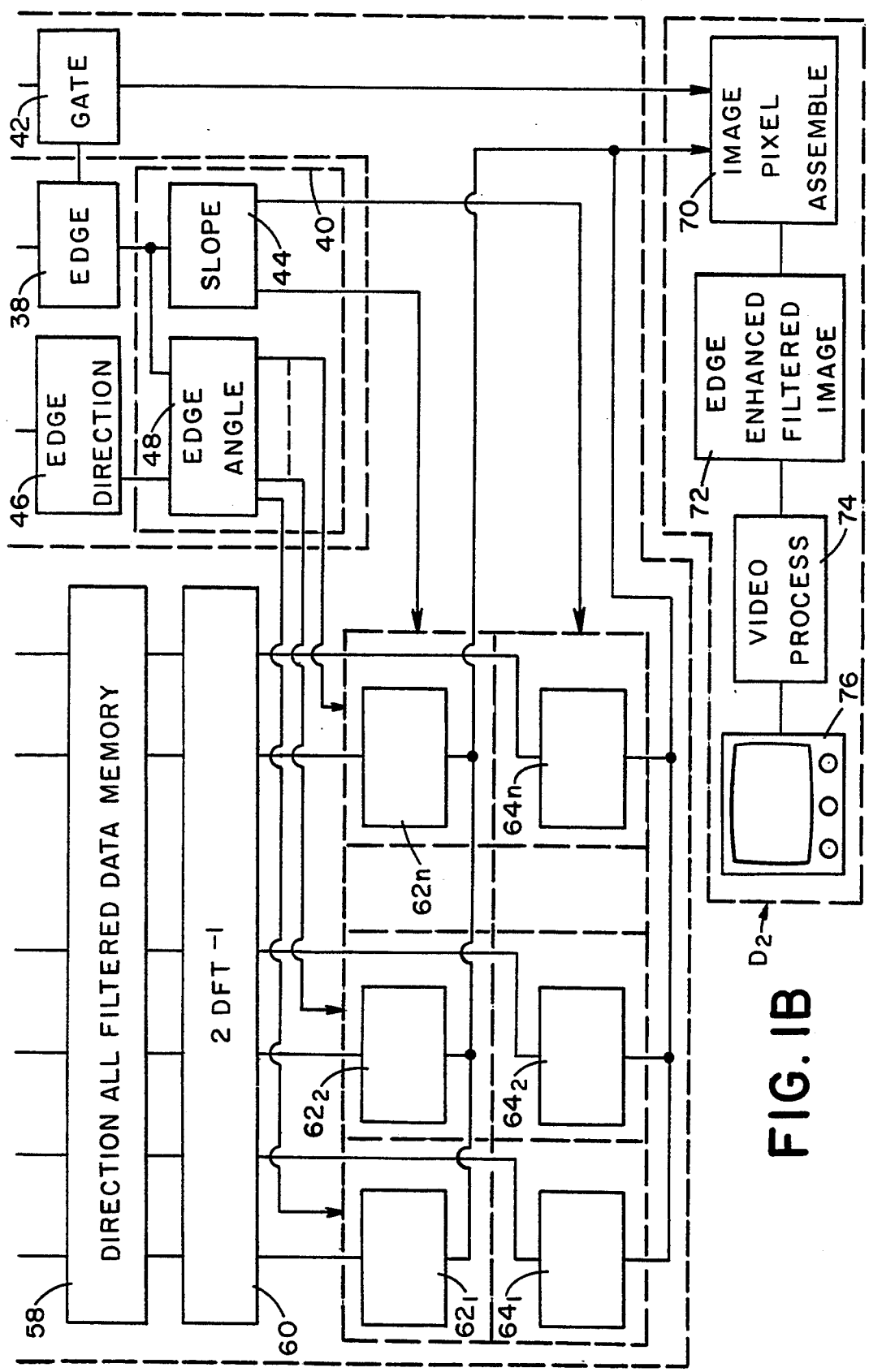

With reference to the FIGS. 1A and 1B, a magnetic resonance imaging system A examines a selected region of a subject and generates an image representation thereof. A first filtering means B filters the resultant image representation, preferably with a smoothing function. An edge enhancement means C enhances the edges of the filtered image for a crisper, more distinct image. More specifically, the edge enhancement means C includes an edge detecting means $C_1$ which determines edge characteristics, such as direction, location, standard deviation or slope, and the like, and selects data filtered with a corresponding one of an array of directionally-dependent filter functions $C_2$ in accordance with the edge determination. An image assembling means D assembles a filtered and edge enhanced image representation from the filtered and edge enhanced image data.

More specifically, the magnetic resonance imaging scanner system A of the preferred embodiment includes a conventional magnetic resonance scanner 10. The magnetic resonance scanner includes the appropriate coils and supporting electronics for generating a substantially uniform main magnetic field through an imaging region. Radio frequency coils and supporting electronics selectively broadcast radio frequency pulses into the imaging region to induce resonance of selected dipoles and manipulate the induced resonance. Gradient field coils and supporting electronics cause gradient magnetic field pulses across the imaging region to provide phase and frequency encoding in the excited resonance and for defining slices or volumes.

Magnetic resonance echo signals or other electronic diagnostic data is collected in a data memory means 12. A reconstruction means b4 such as a two-dimensional inverse Fourier transform, reconstructs the image data from the data memory b2 into an image representation which is stored in an image memory 16. It is to be appreciated that the present invention is applicable to images from sources other than MRI scanners.

The first filter means B performs a smoothing or filtering process on the image. In the preferred embodiment, an 11×11 neighborhood is smoothed. A neighborhood selecting means 20 selects the 11×11 or other proximate neighborhood for each pixel. A comparing means 22 compares each pixel in the neighborhood with the selected centered pixel. The comparing means gates or conveys 24 each pixel that is within a preselected range of the center pixel, e.g. ±5%, to an averaging means 26. This process is repeated to replace each pixel from image memory be with the corresponding average in a filtered image memory 30. In this manner, the image from image memory be is filtered and loaded into the filtered image memory 30. Other filtering processes, such as the one described in U.S. Pat. No. 4,761,819 to Denison, et al. As described in the Denison, et al. may also be used. Of course, images from other sources and magnetic resonance imaging scanners may also have their edges enhanced in accordance with the present invention. These other images may be filtered with smoothing filters such as smoothing filter B or not, as may be appropriate from the nature of the data.

The edge enhancement means C includes a sampling means 32 for sampling each pixel of the filtered image representation in memory 30 along with the adjacent pixel values. Typically, the pixel value and the eight immediately surrounding pixel values in a first concentric ring or the twenty-four adjacent pixel values in the two most closely adjacent concentric rings are sampled. The edge detecting means $C_1$ includes a means for generating a standard deviation image 34 from these nine or twenty-five pixels. Preferably, an Eigenvector means 36 generates an Eigenvector description of the standard deviation, although changes in rate of change, or the like, can also be measured. The Eigenvector representation inherently points in a direction transverse to the direction of an edge at the sampled pixel and has a magnitude which is proportional to the rate of change, i.e. shows how pronounced the edge is. An edge comparing means 3e determines from the magnitude of the Eigenvector whether the pixel is along an edge. More specifically, when the pixel is not near an edge, the Eigenvector is close to zero. The edge comparing means 38 compares the Eigenvector value with a threshold value that is near zero.

A pixel selecting means 40 selects which pixel is passed to the image assembling means D. If the edge comparing means 38 determines that the sampled pixel is not adjacent an edge, the pixel selecting means 40 enables a gate means 42 to pass the sampled pixel to the image assembly means D. If the pixel is adjacent an edge, then a slope comparing means 44 compares the magnitude of the Eigenvector with one or more reference standards indicative of a large or small deviation across the edge and generates appropriate enable signals to enable correspondingly weakly or strongly filtered image pixels to be selected. For example, the slope comparing means may compare the Eigenvector magnitude with a magnitude that corresponds to a median edge slope found in the processed type of image. If the sampled pixel is proximate to an edge, an edge direction means 46 determines the angular orientation or direction along which the edge extends, i.e. the direction normal to the Eigenvector. An edge angle comparing means 48 compares the angle of the edge with a preselected array of directions corresponding to the directions of preselected directional filters. The comparing means 46 then generates an enable signal to enable the selection of the corresponding pixel from an image filtered with a most nearly corresponding one of the directional filters $C_2$.

Because the preferred directional filters operate in the frequency domain, a transform means 50 transforms the filtered image representation from the filtered image memory 30 into a frequency domain or power spectrum which is stored in a power spectrum memory 52. The frequency data is filtered with each of an array of soft directional filter functions $54_1$-$54_n$. In the preferred embodiment, seventeen otherwise identical filter functions are selected with the angle of their directional smoothing at 10° increments. With eighteen selected filtering directions, each pixel is smoothed with a directional filter that is within ±5° of being parallel to the edge. Of course, a larger number of filters can be provided such that each edge is smoothed more parallel to its direction. In image data in which the edges are equally apt to extend in any direction, the filtering directions are spaced at even increments. Of course, when the image has edges primarily in one direction, such as images of stratified or layered materials, the smoothing directions of the filters may be distributed non-uniformly. That is, the filtering functions may be selected to filter along directions that are displaced by only a couple of degrees in the direction that the edges primarily flow and be selected to filter at 20°, 30°, or larger intervals in directions in which edges are uncommon.

A second, like set of hard directional filters $56_1$, $56_2$, ..., $56_n$ filter the frequency data 52 along preselected directions. In the preferred embodiment, the hard and soft directional filters both filter parallel to the same directions. The hard filter functions differ from the soft filter functions in that the filter function is larger to force the data more strongly towards black or white than the soft filter function, which allows a smoother transition. Although it is preferred that the hard and soft filter functions operate along the same directions, it is contemplated that the filter functions might operate along different directions. For example, the soft filter functions may be along 0°, 10°, 20°..... and the hard filter functions might be along 5°, 15°, 25°, .... As stated above, if there is a priori information about the nature of the data which would show that the crisp or hard and dull or soft edges tend to lie primarily along identifiable axes, possibly along different selectable axes, the filter functions may be oriented accordingly. Suitable directional filters are described in *Digital Picture Processing*, A. Rosenfeld, et al., Sec. 6.4.3 "Selective and Weighted Averaging", pp. 255-264.

Optionally, the directionally filtered data may be stored temporarily in a directionally filtered data memory means 58. A reconstruction means 60 transforms the directionally soft filtered data from the memory 58 into a series of directionally filtered soft edge images stored in a series of soft directionally filtered image memories $62_1$, $62_2$, ..., $62_n$. The directionally hard filtered data is reconstructed into a series of directionally filtered images with hard or crisp edges which are stored in a set of hard directionally filtered image memories $64_1$, $64_2$, .., $64_n$. The reconstruction means 60 performs an inverse of the transform performed by transform means 50 in order to return the data from the frequency domain to the spatial domain. Of course, directional filters with additional degrees of hardness/softness can be provided and the slope comparing means can select among a wider range of slopes.

In the preferred embodiment, the slope comparing means 44 provides an enable signal to either the bank of soft filtered image memories 62 or the bank of hard filtered image memories 64 for each detected edge. In response to the edge direction comparison of each sampled pixel, the edge angle comparing means 4S provides an enable signal to the hard and soft directionally filtered image memories corresponding to the angle closest to the direction of the edge. The one of directionally filtered image memories 62, 64 which is enabled by both the slope comparing means and the edge angle comparing means transfers its pixel value corresponding to the sampled pixel to the assembling means D. This process is repeated pixel by pixel stepping through the filtered image 30.

In the preferred embodiment, a high emphasis filter operation is performed on each of images 62 and 64. A suitable high emphasis filter is based on subtracting the Laplacian from a picture as illustrated and described in *Digital Picture Processing*, A. Rosenreid, et al., Sec. 6.3.3, "High Emphasis Filtering", pp. 245-250, 1982.

The resultant image creating means includes an image pixel assembling means 70 which receives filtered pixel values which are not near an edge from the filtered image memory 30 via the gate means 42 and receives corresponding hard or soft directionally filtered pixel values from image memories 62 or 64 for each pixel which is determined to be proximate to an edge. The image assembling means loads each pixel value into the corresponding memory element of an edge enhanced filtered image memory means 72. A video processing means 74 addresses the edge enhanced filtered image memory means 72 to convert the image information to appropriate video format for display on a video monitor 76. Of course, the edge enhanced filtered image representation may be stored on tape or disk, subjected to further processing, displayed in other ways, or the like.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A magnetic resonance imaging system comprising:
   a scanner for generating phase and frequency encoded magnetic resonance data;
   a reconstruction processor for reconstructing the magnetic resonance data into a diagnostic image of a selected spatial region;
   a filter for smoothing the diagnostic image, the smoothed diagnostic image being defined by a rectangular array of pixels;
   a transform processor for transforming the smoothed diagnostic image into frequency domain data;
   a plurality of directional filters for filtering the frequency domain data to generate a corresponding plurality of directionally filtered data sets, the plurality of directional filters filtering along each of a plurality of directions;
   an inverse transform processor for transforming the plurality of directionally filtered data sets into a corresponding plurality of directionally filtered images of the selected spatial region, the directionally filtered images being filtered in a plurality of directions to enhance edge sharpness parallel to the filtering direction, the directionally filtered images each being defined by a rectangular array of directionally filtered image pixels;
a directionally filtered image emory for storing the plurality of directionally filtered images;
an edge determining means for determining whether each pixel of the smoothed diagnostic image is adjacent an edge and a direction of each adjacent edge;
an edge enhanced filtered image assembler for assembling (i) pixels that are not adjacent an edge from the smoothed diagnostic image and (ii) pixels that are adjacent an edge from the directionally filtered images stored in the directionally filtered image memory into an edge enhanced filtered image memory;
a display for converting the assembled pixels in the edge enhanced filtered image memory into a human-readable diagnostic display of the selected spatial region.

2. An apparatus for smoothing and edge enhancing an initial image representation, the apparatus comprising:
an initial image memory for storing the initial image representation;
a plurality of directional filters for filtering the initial image representation in the initial image memory to generate a corresponding plurality of directionally filtered image representations;
a directionally filtered image memory for storing each of the plurality of directionally filtered image representations, the directionally filtered image memory being connected with the directional filters to receive the plurality of directionally filtered image representations therefrom;
a sampler for sampling each pixel of the initial image representation and its neighboring pixels in the initial image memory;
an edge determining means for determining whether each sampled pixel is proximate to an edge;
an edge direction determining means for determining a direction of the edge to which each sampled pixel is proximate;
an edge enhanced filtered image memory for storing an edge enhanced filtered image representation;
a selector for (i) selecting pixels which are not proximate to an edge from the initial image memory and loading the selected non-edge proximate pixels into the edge enhanced filtered image memory and (ii) for each pixel which is proximate to an edge, selecting a corresponding pixel from one of the directionally filtered image representations in the directionally filtered image memory and loading the selected pixel into the edge enhanced filtered image memory.

3. An apparatus for smoothing and edge enhancing an initial image representation of a selected spatial region, the apparatus comprising:
a first plurality of directional filters for filtering the initial image representation to create soft edges, the first plurality of directional filters generating a corresponding array of soft edge directionally filtered image representations each of the selected spatial region;
a second plurality of directional filters for filtering the initial image representation to create crisp edges, the second plurality of directional filters generating a corresponding array of hard edge directionally filtered image representations each of the selected spatial region;
a memory for storing the array of soft edge directionally filtered image representations and the array of hard edge directionally filtered image representations;
a sampler for sampling each pixel of the initial image representation and its neighboring pixels;
an edge determining means for determining whether each sampled pixel is proximate to an edge;
a means for determining an amount of change over the neighboring pixels neighboring each sampled edge proximate pixel;
a hard/soft edge selector for selecting between the hard and soft edge directionally filtered image representation arrays in accordance with the determined change;
an edge direction determining means for determining a direction of the edge to which each sampled edge proximate pixel is proximate;
an edge direction selector which selects for each edge proximate pixel a corresponding directionally filtered pixel from the directionally filtered image representation of the selected one of the hard and soft edge directionally filtered image representation arrays which was directionally filtered in a direction most closely corresponding to the determined edge direction;
a pixel replacer which replaces each sampled edge proximate pixel with the selected directionally filtered pixel to form an edge enhanced filtered image representation;
a display which converts the edge enhanced filtered image representation into a human viewable image.

4. An apparatus for smoothing and edge enhancing an initial image representation a selected spatial region, the apparatus comprising:
a transform which transforms the initial image representation with a first transform function into frequency domain data;
a plurality of directional filters for filtering the frequency domain data to generate a plurality of sets of directionally filtered frequency domain data;
an inverse transform which transforms the directionally filtered frequency domain data sets into a corresponding plurality of directionally filtered image representations of the selected spatial region each filtered with respect to a different direction;
a directionally filtered image memory for storing the plurality of directionally filtered image representations;
a sampling means for sampling each pixel of the initial image representation and its neighboring pixels;
an edge detector for determining whether each sampled pixel is proximate to an edge and a direction of the edge to which each sampled pixel is proximate;
a selecting means for selecting for each pixel determined to be proximate to an edge the corresponding pixel from one of the plurality of directionally filtered image representations which was directionally filtered in a direction most closely corresponding to the determined edge direction;
an assembler for assembling (i) pixels of the initial image representation which are determined not to be proximate to an edge and (ii) the selected pixels from each of the plurality of directionally filtered image representations into an edge enhanced filtered image representation;

a monitor which converts the edge enhanced filtered image representation into a human readable display of the selected region.

5. The apparatus as set forth in claim 4 further including a smoothing filter means for filtering the initial image representation with a smoothing filter.

6. The apparatus as set forth in claim 5 further including a gate means for assembling each sampled pixel that is not adjacent an edge into the edge enhanced filtered image representation.

7. The apparatus as set forth in claim 6 wherein the edge detector includes a means for determining an amount of deviation the pixels neighboring the sampled pixel and a comparer for comparing the determined amount of deviation with a preselected threshold, deviation in excess of the preselected threshold being indicative of a proximate edge and deviation less than the preselected threshold being indicative of the absence of a proximate edge.

8. The apparatus as set forth in claim 7 further including a means for comparing the amount of deviation with a standard, amounts of deviation less than the standard being indicative of a soft or gradual proximate edge and amounts of deviation greater than the second standard being indicative of a hard or sharp proximate edge.

9. The apparatus as set forth in claim 8 wherein the plurality of filters include a plurality of soft edge directional filter functions and a plurality of hard edge directional filter functions to create a plurality of soft edge directionally filtered data sets and a plurality of hard edge directionally filtered data sets, the inverse transform transforming the soft edge directionally filtered data sets into the array of soft edge directionally filtered image representations that are stored in an array of soft edge directionally filtered image memory and transforming the hard edge directionally filtered data sets into the array of hard edge directionally filtered image representations that are stored in an array of hard edge directionally filtered image representation memory, the means for determining the amount of deviation enabling one of the array of hard edge directionally filtered image memories and (ii) the array of soft edge directionally filtered image memories to be addressed by the selecting means.

* * * * *